(12) United States Patent
Sims et al.

(10) Patent No.: US 11,607,267 B2
(45) Date of Patent: Mar. 21, 2023

(54) ELECTROSURGICAL FORCEPS

(71) Applicant: COVIDIEN LP, Mansfield, MA (US)

(72) Inventors: Grant T. Sims, Boulder, CO (US);
Daniel W. Mercier, Erie, CO (US);
Craig V. Krastins, Arvada, CO (US);
Jennifer L. Rich, Parker, CO (US);
Kelley D. Goodman, Erie, CO (US)

(73) Assignee: Covidien LP, Mansfield, MA (US)

( * ) Notice: Subject to any disclaimer, the term of this patent is extended or adjusted under 35 U.S.C. 154(b) by 908 days.

(21) Appl. No.: 16/435,770

(22) Filed: Jun. 10, 2019

(65) Prior Publication Data

US 2020/0383719 A1    Dec. 10, 2020

(51) Int. Cl.
*A61B 18/14* (2006.01)
*A61B 18/00* (2006.01)
*A61B 17/00* (2006.01)
*A61B 17/28* (2006.01)

(52) U.S. Cl.
CPC ........ *A61B 18/1442* (2013.01); *A61B 17/282* (2013.01); *A61B 2017/00438* (2013.01); *A61B 2017/2845* (2013.01); *A61B 2018/0063* (2013.01); *A61B 2018/0094* (2013.01); *A61B 2018/00589* (2013.01); *A61B 2018/00595* (2013.01)

(58) Field of Classification Search
CPC .............. A61B 18/1442; A61B 18/149; A61B 2017/00438
See application file for complete search history.

(56) References Cited

U.S. PATENT DOCUMENTS

| | | |
|---|---|---|
| D249,549 S | 9/1978 | Pike |
| 4,200,104 A | 4/1980 | Harris |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |

(Continued)

FOREIGN PATENT DOCUMENTS

| | | |
|---|---|---|
| CN | 201299462 Y | 9/2009 |
| DE | 2415263 A1 | 10/1975 |

(Continued)

OTHER PUBLICATIONS

U.S. Appl. No. 13/731,674, filed Dec. 31, 2012; inventor: Siebrecht.

(Continued)

*Primary Examiner* — Joseph A Stoklosa
*Assistant Examiner* — Marina Delaney Templeton
(74) *Attorney, Agent, or Firm* — Carter, DeLuca & Farrell LLP

(57) ABSTRACT

An electrosurgical forceps includes first and second shaft members pivotably coupled to one another such that pivoting of the first and second shaft members between spaced-apart and approximated positions pivots jaw members thereof between open and closed positions. A proximal end portion of the second shaft member may be pivoted against a resilient bias of a spring element to apply a predetermined clamping pressure on tissue and ultimately engage an activation switch to delivery electrosurgical energy to the clamped tissue.

15 Claims, 3 Drawing Sheets

(56) References Cited

U.S. PATENT DOCUMENTS

| | | | |
|---|---|---|---|
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,626,607 A * | 5/1997 | Malecki | A61B 17/00234 606/205 |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| 6,270,497 B1 * | 8/2001 | Sekino | A61B 18/14 606/49 |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,628,791 B2 * | 12/2009 | Garrison | A61B 18/1445 606/171 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 8,409,246 B2 * | 4/2013 | Kerr | A61B 18/1206 606/206 |
| 8,430,877 B2 * | 4/2013 | Kerr | A61B 17/282 606/51 |
| 8,974,447 B2 * | 3/2015 | Kimball | A61B 17/320092 606/27 |
| 9,084,608 B2 | 7/2015 | Larson et al. | |
| 9,211,657 B2 | 12/2015 | Ackley et al. | |
| 9,375,256 B2 | 6/2016 | Cunningham et al. | |
| 9,375,262 B2 | 6/2016 | Reschke et al. | |
| 9,439,717 B2 | 9/2016 | Orszulak et al. | |
| 9,445,865 B2 | 9/2016 | Sartor et al. | |
| 9,456,863 B2 | 10/2016 | Moua | |
| 9,468,453 B2 | 10/2016 | Hart et al. | |
| 9,474,570 B2 | 10/2016 | McKenna et al. | |
| 9,492,225 B2 | 11/2016 | Dycus et al. | |
| 9,539,053 B2 | 1/2017 | Hixson et al. | |
| 9,554,845 B2 | 1/2017 | Arts | |
| 9,579,117 B2 | 2/2017 | Kappus et al. | |
| 9,579,146 B2 | 2/2017 | Johnson et al. | |
| 9,585,716 B2 | 3/2017 | Johnson et al. | |
| 9,622,810 B2 * | 4/2017 | Hart | A61B 34/76 |
| 9,642,671 B2 | 5/2017 | Lee et al. | |
| 9,655,673 B2 | 5/2017 | McCullough, Jr. et al. | |
| 9,713,491 B2 | 7/2017 | Roy et al. | |
| 9,717,548 B2 | 8/2017 | Couture | |
| 9,770,288 B2 | 9/2017 | Gilbert | |
| 9,795,402 B2 | 10/2017 | Allen, IV et al. | |
| 9,877,775 B2 | 1/2018 | Hart | |
| 9,943,357 B2 | 4/2018 | Cunningham et al. | |
| 10,004,527 B2 * | 6/2018 | Gee | A61B 17/320068 |
| 10,058,346 B2 * | 8/2018 | Messerly | A61B 17/2816 |
| 10,070,916 B2 | 9/2018 | Artale | |
| 10,231,772 B2 | 3/2019 | Duffin et al. | |
| 10,265,119 B2 | 4/2019 | Kharin et al. | |
| 10,405,874 B2 | 9/2019 | Twomey et al. | |
| 10,588,686 B2 * | 3/2020 | Allen, IV | A61B 90/08 |
| 10,973,567 B2 * | 4/2021 | Sims | A61B 18/12 |
| 11,039,848 B2 * | 6/2021 | Asher | A61B 17/320092 |
| 11,116,532 B2 * | 9/2021 | Asher | A61B 17/320092 |
| 2005/0113827 A1 | 5/2005 | Dumbauld et al. | |
| 2005/0283148 A1 | 12/2005 | Janssen et al. | |
| 2007/0078458 A1 | 4/2007 | Dumbauld et al. | |
| 2008/0215048 A1 * | 9/2008 | Hafner | A61B 18/1442 606/42 |
| 2008/0287948 A1 | 11/2008 | Newton et al. | |
| 2011/0028964 A1 | 2/2011 | Edwards | |
| 2012/0059371 A1 | 3/2012 | Anderson et al. | |
| 2012/0095456 A1 | 4/2012 | Schechter et al. | |
| 2013/0018411 A1 * | 1/2013 | Collings | A61B 17/282 606/205 |
| 2013/0296843 A1 * | 11/2013 | Boudreaux | A61B 18/18 606/33 |
| 2014/0221994 A1 | 8/2014 | Reschke | |
| 2014/0221995 A1 | 8/2014 | Guerra et al. | |
| 2014/0250686 A1 | 9/2014 | Hempstead et al. | |
| 2014/0353188 A1 | 12/2014 | Reschke et al. | |
| 2015/0018816 A1 | 1/2015 | Latimer | |
| 2015/0032106 A1 | 1/2015 | Rachlin | |
| 2015/0066026 A1 | 3/2015 | Hart et al. | |
| 2015/0088122 A1 | 3/2015 | Jensen | |
| 2016/0175033 A1 * | 6/2016 | Le | A61B 18/1442 606/51 |
| 2018/0132888 A1 * | 5/2018 | Asher | A61B 17/320092 |
| 2018/0228531 A1 | 8/2018 | Cunningham et al. | |
| 2018/0296213 A1 * | 10/2018 | Strobl | A61B 18/1445 |
| 2019/0133674 A1 * | 5/2019 | Singh | A61B 18/1442 |
| 2020/0069362 A1 * | 3/2020 | Paesch | A61B 18/1445 |
| 2020/0229836 A1 * | 7/2020 | Yanagi | A61B 18/1445 |

FOREIGN PATENT DOCUMENTS

| | | |
|---|---|---|
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |

(56) References Cited

FOREIGN PATENT DOCUMENTS

| | | |
|---|---|---|
| DE | 10045375 A1 | 4/2002 |
| DE | 20121161 U1 | 4/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 A | 5/1986 |
| JP | 1024051 | 1/1989 |
| JP | 1147150 | 6/1989 |
| JP | 55106 | 1/1993 |
| JP | 0540112 A | 2/1993 |
| JP | 6121797 | 5/1994 |
| JP | 6285078 A | 10/1994 |
| JP | 06343644 | 12/1994 |
| JP | 6511401 A | 12/1994 |
| JP | 07265328 | 10/1995 |
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 09000538 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | 0006030945 B2 | 11/2016 |
| JP | 6502328 B2 | 4/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" . Current Surgical Techniques in Urology, vol. 14, Issue 3, 2001.

(56) References Cited

OTHER PUBLICATIONS

Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy" FIGO 2000, Washington, D.C..
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed 12117/2008; inventor: Paul R. Sremeich.

* cited by examiner

ELECTROSURGICAL FORCEPS

BACKGROUND

The disclosure relates to electrosurgical instruments and, more particularly, to electrosurgical forceps for grasping, treating, and/or dividing tissue.

TECHNICAL FIELD

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue. Typically, once tissue is treated, the surgeon has to accurately sever the treated tissue. Accordingly, many electrosurgical forceps incorporate a knife configured to effectively sever tissue after the tissue is treated.

The surgical forceps generally includes a pair of shaft members having jaws attached to distal ends thereof. A compressible switch may be provided at a proximal end of the one of the shaft members. During clamping of tissue between the jaws, one or both of the shaft members flex toward one another, whereby the proximal end of one shaft member actuates the switch at the proximal end of the other of the shaft members.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about +/−10 degrees from true parallel and true perpendicular.

An electrosurgical forceps provided in accordance with aspects of the disclosure includes a first shaft member, a second shaft member, and a biasing member. The first shaft member includes an inner frame having a first jaw member secured to and extending distally therefrom, an outer housing surrounding at least a portion of the inner frame, and a lever supported by the outer housing and configured to engage a proximal end portion of the inner frame. The second shaft member is pivotably coupled to the first shaft member and has a second jaw member secured to and extending distally from the second shaft member. The biasing member is operably engaged with the lever. The lever is configured to pivot against a resilient bias of the biasing member to pivot the inner frame and, in turn, pivot the first jaw member toward the second jaw member.

In aspects, the lever may include a handle protruding out from the outer housing.

In aspects, the handle may define a finger-retaining portion.

In aspects, the lever may be pivotably coupled to the outer housing.

In aspects, the lever may have a proximal end portion engaged with the biasing member, and a distal end portion configured to engage the proximal end portion of the inner frame.

In aspects, the lever may be pivotably coupled to the outer housing via a pivot point disposed between the biasing member and the handle.

In aspects, the biasing member may be disposed proximally of the pivot point.

In aspects, the handle may be disposed distally of the pivot point.

In aspects, the inner frame may be configured to rotate in a first direction in response to a rotation of the lever in a second direction, opposite the first direction.

In aspects, the biasing member may be configured to compress or extend, between the outer housing and the lever, in response to the lever pivoting against the resilient bias of the biasing member.

In aspects, the second shaft member may be rigid along a length thereof.

In aspects, the first and second shaft members may be configured to resist flexing during approximation of the first and second jaw members.

In aspects, the lever may be pivotably coupled to the proximal end portion of the inner frame.

In aspects, the lever, the inner frame, and the outer housing of the first shaft member may be configured to pivot together upon an application of a first threshold force to the lever. The lever may be configured to pivot relative to the inner frame and the outer housing upon an application of a second threshold force to the lever, greater than the first threshold force.

In aspects, the biasing member may be disposed between the proximal end portion of the inner frame and a distal end portion of the lever, such that rotation of the lever relative to the inner frame expands or compresses the biasing member.

In aspects, the biasing member may be received in a cavity defined in the proximal end portion of the inner frame and may be engaged with the distal end portion of the lever.

In aspects, the distal end portion of the lever may be received in the cavity of the inner frame.

In accordance with another aspect of the disclosure, an electrosurgical forceps is provided and includes a first jaw member, a first shaft member pivotably coupled to the first jaw member, a second shaft member pivotably coupled to the first shaft member, and a biasing member configured to engage the first shaft member. The second shaft member has a second jaw member secured to and extending distally from the second shaft member. A rotation of the first shaft member is configured to pivot the first jaw member toward the second jaw member. An application of a threshold rotational force on the first shaft member overcomes a resilient bias of the biasing member to pivot the first shaft member relative to the first jaw member.

In aspects, the biasing member may be a leaf spring having an end fixed to the first jaw member.

In aspects, the first shaft member may have a distal end portion engaged with the biasing member.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
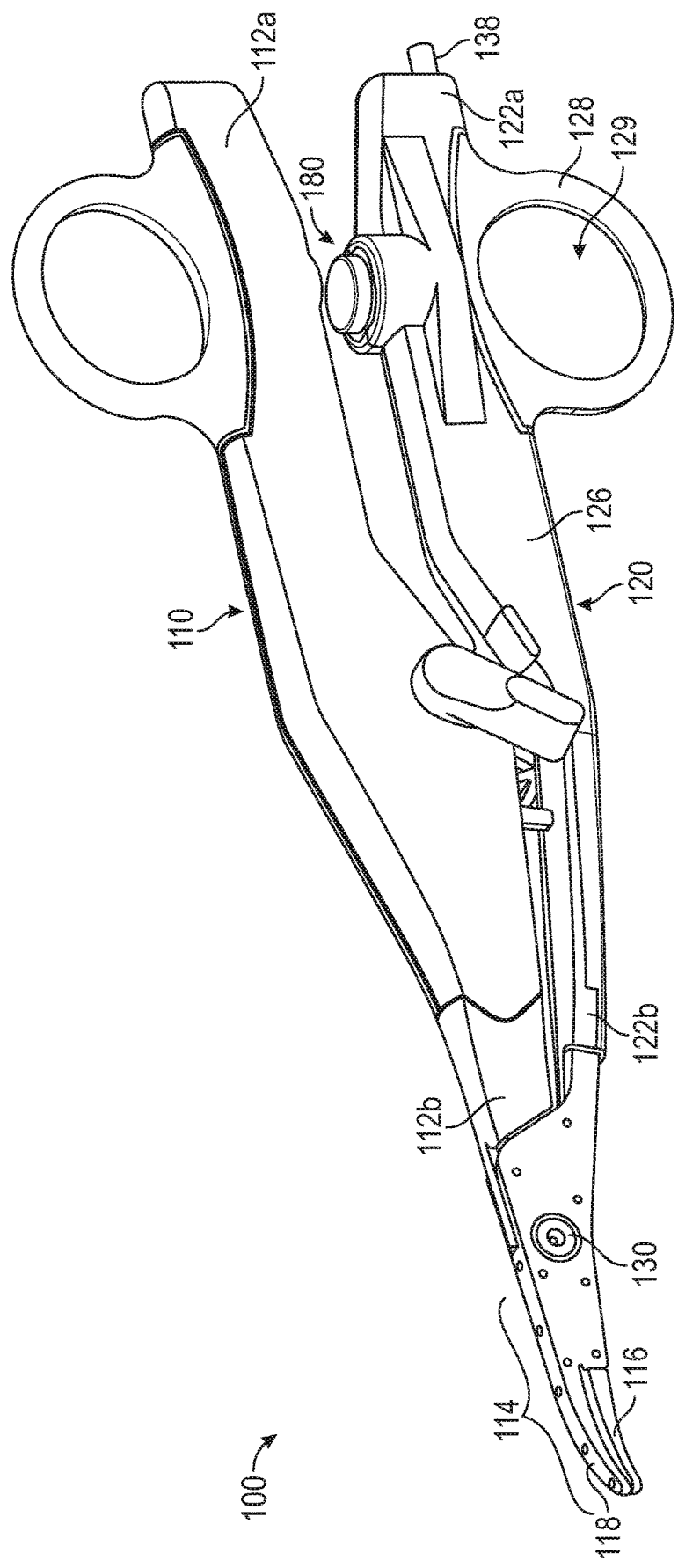
FIG. 1 is a side, perspective view of an electrosurgical forceps provided in accordance with aspects of the disclosure.

Referring to FIG. 1, a forceps 100 provided in accordance with the disclosure generally includes first and second shaft members 110, 120 and an end effector assembly 114. Shaft members 110, 120 each have a proximal end portion 112a, 122a and a distal end portion 112b, 122b. End effector assembly 114 includes first and second jaw members 116, 118 extending from distal end portions 112b, 122b of shaft members 110, 120, respectively. Forceps 100 further includes a pivot member 130 pivotably coupling first and second shaft members 110, 120 with one another, such that an approximation of the proximal end portion 112a, 122a of the shaft member 110, 120 approximates the first and second jaw members 210, 220.

A switch assembly 180 is coupled to the shaft member 120 and enables the selective supply of electrosurgical energy to end effector assembly 114. An electrosurgical cable 138 electrically couples forceps 100 to a source of energy (not shown), e.g., an electrosurgical generator, to enable the supply of electrosurgical energy to jaw members 116, 118 of end effector assembly 114 upon activation of the switch assembly 180.

Figure 2:
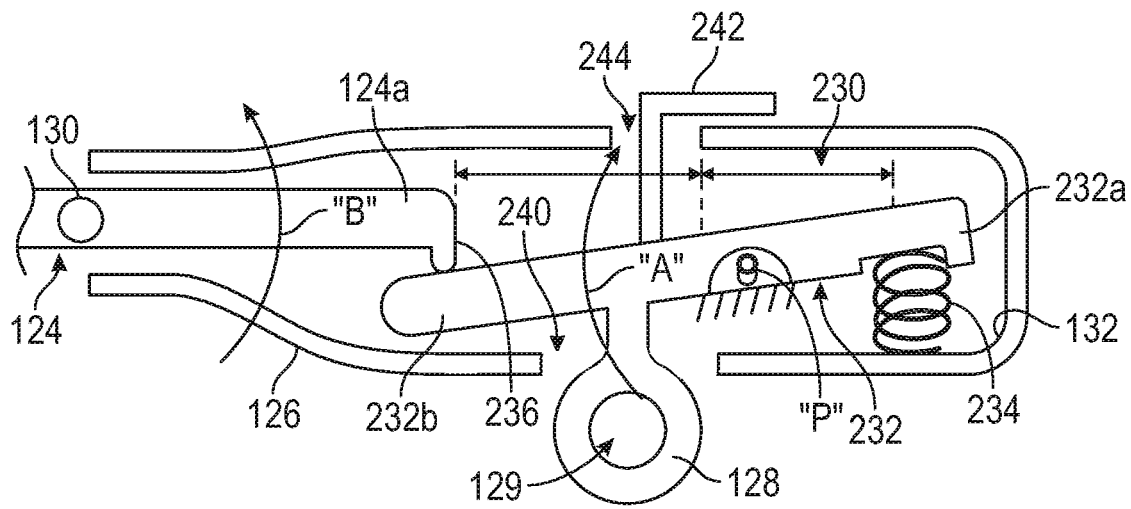
FIG. 2 is a side, schematic view of a proximal end portion of a first shaft member of the forceps of FIG. 1, with an outer housing of the first shaft member removed to illustrate internal components therein.

With reference to FIGS. 1 and 2, the second shaft member 120 includes an inner frame 124 and an outer housing 126 surrounding at least a portion of the inner frame 124. The outer housing 126 encloses and/or operably supports the internal components disposed within the shaft member 120. More specifically, outer housing 126 of shaft member 120 encloses and supports at least a portion of inner frame 124 and receives electrosurgical cable 138.

With reference to FIG. 2, the second shaft member 120 includes a jaw force control assembly 230 at least partially received in the outer housing 126. The jaw force control assembly 230 generally includes a lever 232 operably engaged with a proximal end portion 124a of the inner frame 124 and a biasing member 234 disposed between the lever 232 and the outer housing 126. The lever 232 has an elongated configuration and extends between a proximal end portion 232a and a distal end portion 232b. The proximal end portion 232a of the lever 232 is pivotably coupled to the outer housing 126. The distal end portion 232b of the lever 232 is engaged with the proximal end portion 124a of the inner frame 124. The inner frame 124 includes a protuberance 236 in sliding engagement with the distal end portion 232b of the lever 232. In aspects, instead of a protuberance 236, the inner frame 124 may have a pin and cam slot connection with the distal end portion 232b of the lever 232. The lever 232 has a handle 128 extending from the distal end portion 232b thereof and out through an opening 240 defined in the outer housing 126. The handle 128 defines a finger retaining portion, such as, for example, a round hole 129 configured to facilitate grasping and manipulating shaft member 120.

The biasing member 234 is received in the outer housing 126 between the proximal end portion 232a of the lever 232 and an inner surface 132 of the outer housing 126. The biasing member 234 is disposed proximally of a pivot point "P" of the lever 232, whereas the handle 128 is disposed distally of the pivot point "P" of the lever 232. The biasing member 234 may be any suitable spring element, such as, for example, a compression spring or an extension spring. The biasing member 234 is configured to resist rotation of the lever 232 relative to the inner frame 124 and the outer housing 126 during an initial approximation of the proximal end portions 112a, 122a of the first and second shaft members 110, 120.

Upon an application of an approximating force to the handle 128 sufficient to exceed a threshold force, the biasing member 234 is configured to compress, thereby allowing the lever 232 to pivot relative to the inner frame 124 and the outer housing 126 to apply an additional sealing force to the end effector assembly 114 (FIG. 1). The lever 232 may further include an appendage 242, such as, for example, a post, protruding therefrom and out of another opening 244 in the outer housing 126. The post 242 is configured to engage the activation switch 180 upon fully approximating the end effector assembly 114. In other aspects, the activation switch 180 may be coupled to the lever 232 whereas the post 242 may be coupled to the shaft member 120.

In operation, with tissue disposed between the jaws 116, 118, the proximal end portions 112a, 122a of the first and second shaft members 110, 120 are approximated by applying a threshold force on the handles 128 of the first and second shaft members 110, 120. As the proximal end portions 112a, 122a approximate, likewise do the jaw members 116, 118 to compress the tissue therebetween. The first and second shaft members 110, 120 may be substantially rigid along their lengths so as to resist flexing during approximation. With the tissue compressed between the jaw members 116, 118, a higher force may be necessary to continue to approximate the proximal end portions 112a, 122a of the shaft members 110, 120 and/or to approximate the jaw members 114, 116.

Upon the application of a threshold force on the handle 128 of the second shaft member 120, the biasing member 234 begins to compress under a force applied by the proximal end portion 232a of the lever 232. As the lever 232 begins to rotate within the outer housing 126 in the direction indicated by arrow "A" in FIG. 2, the distal end portion 232b of the lever 232 drives rotation of the inner frame 124 of the second shaft member 120 in a second direction indicated by arrow "B" in FIG. 2. As the inner frame 124 rotates, the gap defined between the jaw members 116, 118 further closes to apply a predetermined, constant clamping pressure on the tissue dictated by the spring constant of the biasing member 234. Eventually, a further approximation of the proximal end portions 112a, 122a causes the appendage 242 of the lever 232 to actuate the activation switch 180 to deliver electrosurgical energy to the tissue.

In another aspect, instead of the pivot point "P" being disposed between the biasing member 234 and the distal end portion 232b of the lever 232, the distal end portion 232b of the lever 232 may be pivotably coupled to the housing 126 and/or to rigid leg 124 with the biasing member 234 disposed adjacent the proximal end portion 232a of the lever 232 or between the proximal and distal end portions 232a, 232b of the lever 232. This may result in an overall shorter jaw force control assembly 230. In this alternate embodiment, the distal end portion 232b of the lever 232 may remain out of engagement with the proximal end portion 124a of the inner frame 124 throughout approximation of the proximal end portions 112a, 122a of the first and second shaft members 110, 120.

In yet another aspect, the handle 128 may be non-pivotably coupled to the housing 126 while being permitted to slide axially along a transverse axis relative to the longitudinal axis of the shaft member 120. The biasing member 234 may be coaxial with the transverse axis and captured between the handle 128 and the housing 126. An activation switch, such as, for example, the activation switch 180 (FIG. 1), may be attached to an opposite end of the handle 128 and configured to move with the handle 128 along the transverse axis. Upon achieving a threshold sealing force with the jaw members 116, 118, an application of a clamping pressure on the handle 128 will overcome the resilient bias of the biasing member 234 to allow the handle 128 to slide within the housing 126 to activate the switch 180.

Figure 3:
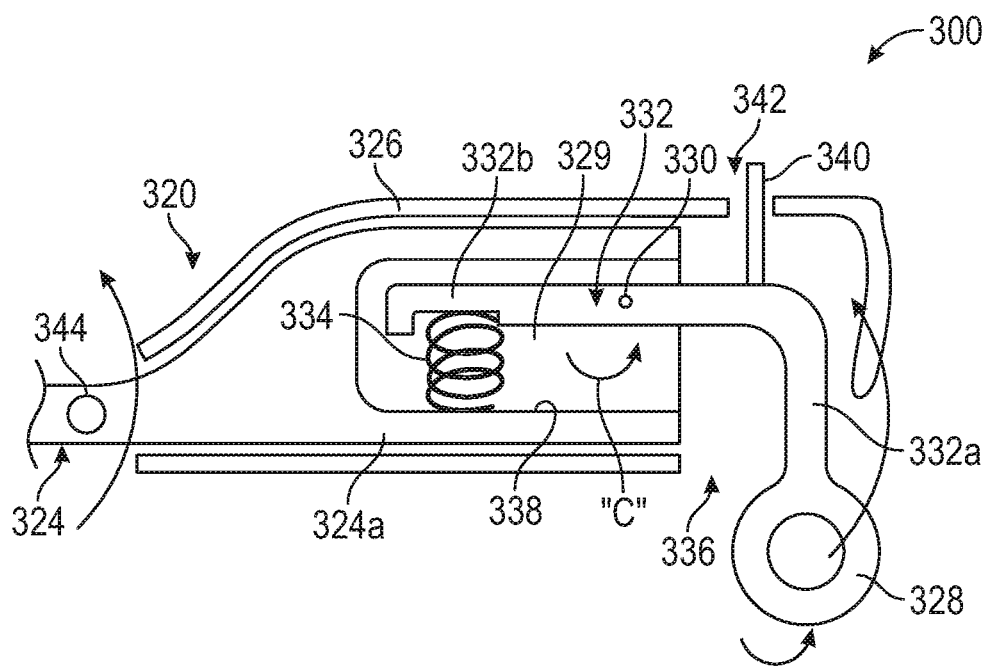
FIG. 3 is a side, schematic view of a proximal end portion of a first shaft member of another embodiment of an electrosurgical forceps, with an outer housing of the first shaft member removed to illustrate internal components therein.

FIG. 3 illustrates a shaft member 320 of another embodiment of an electrosurgical forceps 300. The forceps 300 is similar to the forceps 100 of FIGS. 1 and 2 and will only be described in detail to describe differences between the two. The shaft member 320 of the forceps 320 has an outer housing 326, an inner frame 324 disposed in the outer housing 326, and a lever 332. The inner frame 324 has a proximal end portion 324a defining a cavity 329 therein. The lever 332 has a proximal end portion 332a defining a handle 328 that protrudes from an opening 336 in the outer housing 326, and a distal end portion 332b received in the cavity 329 of the inner frame 324. The lever 332 is pivotably coupled to the proximal end portion 324a of the inner frame 324 about a pivot point 330.

The first shaft member 320 further includes a biasing member 334 received in the cavity 329 and captured between the distal end portion 332b of the lever 332 and an inner surface 338 of the inner frame 324. The biasing member 334 is configured to resist rotation of the lever 332 relative to the inner frame 324 in a first rotational direction, indicated by arrow "C" in FIG. 3. The lever 332 further includes a post 340 extending therefrom and out of another opening 342 in the outer housing 326. The post 340 is configured to actuate the activation switch 180 (FIG. 1) upon fully approximating the jaw members 116, 118 about tissue.

In operation, to clamp tissue with the forceps 300, a force is applied to the handle 328 to pivot the lever 332 along with the inner frame 324 and outer housing 326 about a pivot point 344. Upon the application of a threshold force on the handle 328 of the first shaft member 320, the biasing member 334 begins to compress under a force applied by the distal end portion 332b of the lever 332. As the lever 332 begins to rotate within the outer housing 326 and relative to the inner frame 324, in the direction indicated by arrow "C" in FIG. 3, the biasing member 334 causes the end effector assembly, such as, for example, the end effector assembly 114 (FIG. 1), to apply a predetermined, constant clamping pressure on tissue. The spring constant of the biasing member 334 may be selected to apply a desired clamping pressure on the tissue. Eventually, the post 340 of the lever 332 contacts the activation switch 180 (FIG. 1) to deliver electrosurgical energy to the tissue.

Figure 4:
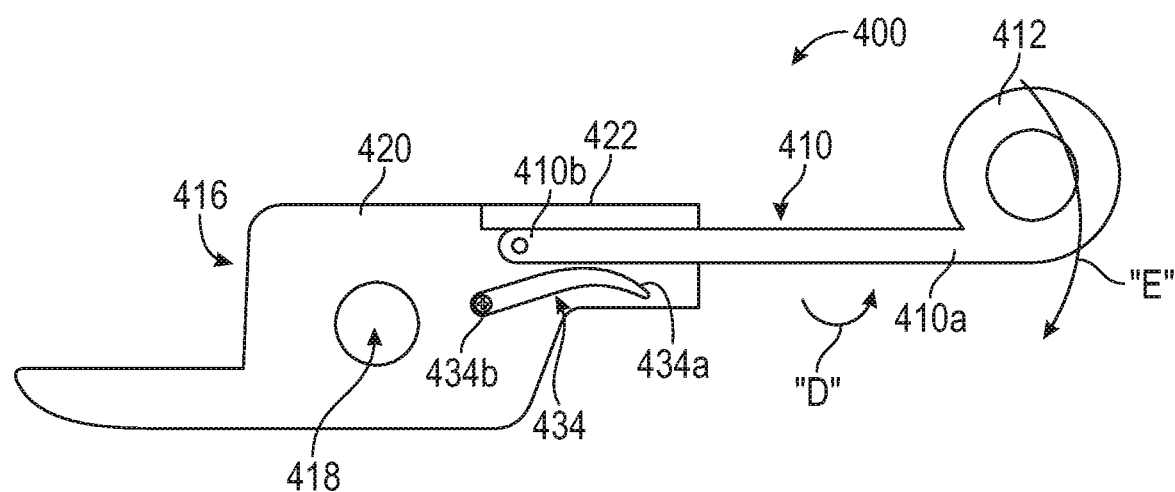
FIG. 4 is a side, schematic view illustrating components of a first shaft member and a first jaw member of another embodiment of an electrosurgical forceps.

FIG. 4 illustrates a first shaft member 410 and a first jaw member 416 of another embodiment of an electrosurgical forceps 400. The forceps 400 is similar to the forceps 100 of FIGS. 1 and 2 and will only be described in detail to describe differences between the two embodiments. The first shaft member 410 has a proximal end portion 410a defining a handle 412 and a distal end portion 410b pivotably coupled to the first jaw member 416. In aspects, the distal end portion 410b of the first shaft member 410 may be pivotably attached to any suitable location of the forceps 400, such as an outer housing (not explicitly shown) of the first shaft member 410.

The first jaw member 416 defines a pivot opening 418 configured to receive a pivot pin (not explicitly shown) for pivotably coupling the first jaw member 416 to a second jaw member (not explicitly shown). The first jaw member 416 has a proximal flange 420 extending proximally therefrom. The proximal flange 420 has a stop 422 protruding inwardly and abutting the distal end portion 410b of the first shaft member 410. As such, the distal end portion 410b of the first shaft member 410 is prevented from rotation in a first direction, indicated by arrow "D" in FIG. 4, and allowed to rotate in a second direction, indicated by arrow "E" in FIG. 4.

The forceps 400 further includes a biasing member 434, such as, for example, a leaf spring, a coned-disc spring, or a stack of coned-disc springs. In aspects, the biasing member 434 may be any suitable spring element. The biasing member 434 has a distal end 434b fixed to the proximal flange 420 and a free proximal end 434a. The distal end portion 410b of the first shaft member 410 is engaged with the proximal end 434a of the biasing member 434. In aspects, the distal end portion 410b of the first shaft member 410 and the distal end 434b of the biasing member 434 may be pivotably coupled to the proximal flange 420 at the same pivot point.

In operation, to clamp tissue with the forceps 400, a force is applied to the handle 412 to pivot the shaft member 410 along with the jaw member 416 about the pivot opening 418. Upon the application of a threshold force on the handle 412 of the first shaft member 410, the biasing member 434 begins to bend or rotate under a force applied by the distal end portion 410b of the shaft member 410. As the first shaft member 410 begins to rotate relative to the proximal flange 420, in the direction indicated by arrow "E" in FIG. 4, the biasing member 434 causes the end effector assembly, such as, for example, the end effector assembly 114 (FIG. 1) to apply a predetermined, constant clamping pressure on the tissue. The spring constant of the biasing member 434 may be selected to apply a desired clamping pressure on the tissue. Eventually, the handle 412 of the first shaft member 410 contacts the activation switch 180 (FIG. 1) to deliver electrosurgical energy to the tissue.

In aspects, any of the biasing members disclosed herein may be preloaded.

For a detailed description of various components and manners of operating the forceps of the disclosure, reference may be made to U.S. Patent Application Publication No. 2018/0325,580, filed on May 12, 2017, the entire contents of which are incorporated by reference herein.

The various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416 (now U.S. Pat. No. 8,828,023), and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
   a first shaft member including:
      an inner frame having a first jaw member secured to and extending distally therefrom;
      an outer housing surrounding at least a portion of the inner frame; and
      a lever supported by the outer housing and configured to engage a proximal end portion of the inner frame;
   a second shaft member pivotably coupled to the first shaft member and having a second jaw member secured to and extending distally from the second shaft member; and
   a biasing member operably engaged with the lever, the lever configured to pivot against a resilient bias of the biasing member to pivot the inner frame and, in turn, pivot the first jaw member toward the second jaw member, wherein the lever, the inner frame, and the outer housing of the first shaft member are configured to pivot together upon an application of a first threshold force to the lever, and the lever is configured to pivot relative to the inner frame and the outer housing upon an application of a second threshold force to the lever, greater than the first threshold force.

2. The electro surgical forceps according to claim 1, wherein the lever includes a handle protruding from the outer housing.

3. The electrosurgical forceps according to claim 2, wherein the handle defines a finger-retaining portion.

4. The electrosurgical forceps according to claim 2, wherein the lever is pivotably coupled to the outer housing.

5. The electrosurgical forceps according to claim 4, wherein the lever has a proximal end portion engaged with the biasing member and a distal end portion configured to engage the proximal end portion of the inner frame.

6. The electrosurgical forceps according to claim 5, wherein the lever is pivotably coupled to the outer housing via a pivot point disposed between the biasing member and the handle.

7. The electrosurgical forceps according to claim 6, wherein the biasing member is disposed proximally of the pivot point.

8. The electrosurgical forceps according to claim 6, wherein the handle is disposed distally of the pivot point.

9. The electro surgical forceps according to claim 1, wherein the inner frame is configured to rotate in a first direction in response to rotation of the lever in a second direction, opposite the first direction.

10. The electrosurgical forceps according to claim 1, wherein the biasing member is configured to compress or extend between the outer housing and the lever in response to the lever pivoting against the resilient bias of the biasing member.

11. The electrosurgical forceps according to claim 1, wherein the second shaft member is rigid along a length thereof.

12. The electrosurgical forceps according to claim 11, wherein the first and second shaft members are configured to resist flexing during approximation of the first and second jaw members.

13. The electrosurgical forceps according to claim 1, wherein the biasing member is disposed between the proximal end portion of the inner frame and a distal end portion of the lever, such that rotation of the lever relative to the inner frame expands or compresses the biasing member.

14. The electrosurgical forceps according to claim 13, wherein the biasing member is received in a cavity defined in the proximal end portion of the inner frame and is engaged with the distal end portion of the lever.

15. The electrosurgical forceps according to claim 14, wherein the distal end portion of the lever is received in the cavity of the inner frame.

* * * * *